US00PP17851P2

(12) United States Plant Patent
Rother

(10) Patent No.: US PP17,851 P2
(45) Date of Patent: Jul. 3, 2007

(54) *OSTEOSPERMUM* PLANT NAMED 'MT. DANDENONG'

(50) Latin Name: *Osteospermum ecklonis*
Varietal Denomination: Mt. Dandenong

(76) Inventor: Roy Rother, 2/6 Winston Dve., Caulfield, Sth.3162 (AU)

( * ) Notice: Subject to any disclaimer, the term of this patent is extended or adjusted under 35 U.S.C. 154(b) by 0 days.

(21) Appl. No.: 11/299,963

(22) Filed: Dec. 12, 2005

(51) Int. Cl.
*A01H 5/00* (2006.01)

(52) U.S. Cl. ..... Plt./360

(58) Field of Classification Search ..... Plt./360
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Osteospermum* plant named 'Mt. Dandenong', characterized by its upright, somewhat outwardly spreading and mounded plant habit; freely branching habit; freely and continuous flowering habit; and inflorescences with light purple-colored ray florets.

1 Drawing Sheet

Botanical designation: *Osteospermum ecklonis.*
Botanical denomination: 'Mt. Dandenong'.

BACKGROUND OF THE INVENTION

The present Invention relates to a new and distinct cultivar of *Osteospermum* plant, botanically known as *Osteospermum ecklonis,* and hereinafter referred to by the name 'Mt. Dandenong'.

The new *Osteospermum* is a product of a planned breeding program conducted by the Inventor in Emerald, Victoria, Australia. The objective of the breeding program was to create new compact and continuous flowering *Osteospermum* cultivars with large and attractive inflorescences.

The new *Osteospermum* originated from a cross-pollination in 1999 of a proprietary *Osteospermum ecklonis* selection identified as code number 4636, not patented, as the female, or seed, parent with a proprietary *Osteospermum ecklonis* selection identified as code number 9537, not patented, as the male, or pollen, parent. The new *Osteospermum* was discovered and selected by the Inventor as a single flowering plant within the progeny of the stated cross-pollination grown in a controlled environment in Emerald, Victoria, Australia in 2000.

Asexual reproduction of the new *Osteospermum* by terminal vegetative cuttings was first conducted in Emerald, Victoria, Australia on Jul. 7, 2000. Asexual reproduction by cuttings has shown that the unique features of this new *Osteospermum* are stable and reproduced true to type in successive generations.

SUMMARY OF THE INVENTION

The cultivar Mt. Dandenong has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Mt. Dandenong'. These characteristics in combination distinguish 'Mt. Dandenong' as a new and distinct *Osteospermum:*

1. Upright, somewhat outwardly spreading and mounded plant habit.
2. Freely branching habit.
3. Freely and continuous flowering habit.
4. Inflorescences with light purple-colored ray florets.

Plants of the new *Osteospermum* differ primarily from plants of the parent selections in plant habit and size and inflorescence size and coloration.

Plants of the new *Osteospermum* can be compared to plants of the cultivar Side Purple, not patented. However, plants of the new *Osteospermum* have larger inflorescences and flower earlier than plants of the cultivar Side Purple. In addition, plants of the new *Osteospermum* have slightly lighter purple-colored ray florets than plants of the cultivar Side Purple.

BRIEF DESCRIPTION OF THE PHOTOGRAPHS

The accompanying colored photographs illustrate the overall appearance of the new *Osteospermum* showing the colors as true as it is reasonably possible to obtain in colored reproductions of this type. Colors in the photographs may differ from the color values cited in the detailed botanical description which accurately describe the colors of the new *Osteospermum.*

The photograph at the top of the sheet is a close-up view of a typical inflorescence of 'Mt. Dandenong'.

The photograph at the bottom of the sheet comprises a side perspective view of a typical flowering plant of 'Mt. Dandenong' grown in a container.

DETAILED BOTANICAL DESCRIPTION

The new *Osteospermum* has not been observed under all possible environmental conditions. The phenotype may vary somewhat with variations in environment such as temperature and light intensity, without, however, any variance in genotype.

The aforementioned photographs, following observations and measurements describe plants grown in Bonsall, Calif. in an outdoor nursery during the summer and under commercial production practices. Plants were about nine weeks from planting rooted young plants when the photographs and description were taken. During the production of the plants, day temperatures ranged from 18° C. to 35° C. and night temperatures ranged from 13° C. to 21° C. In the following description, color references are made to The Royal Horticultural Society Colour Chart, 1995 Edition, except where general terms of ordinary dictionary significance are used.

Botanical classification: *Osteospermum ecklonis* cultivar Mt. Dandenong.

Parentage:

*Female, or seed, parent.*—Proprietary selection of *Osteospermum ecklonis* identified as code number 4636, not patented.

*Male, or pollen, parent.*—Proprietary selection of *Osteospermum ecklonis* identified as code number 9537, not patented.

Propagation:

*Type.*—Terminal vegetative cuttings.

*Time to initiate rooting.*—About two weeks at 20° C.

*Time to produce a rooted young plant.*—About four weeks at 20° C.

*Root description.*—Fine, fibrous; white in color.

*Rooting habit.*—Freely branching.

Plant description:

*Plant form and growth habit.*—Perennial herbaceous container and garden plant. Upright, somewhat outwardly spreading and mounded plant habit; broad inverted triangle. Freely branching habit, about 15 primary lateral branches and numerous secondary lateral branches. Vigorous growth habit.

*Plant height.*—About 34 cm.

*Plant width or area of spread.*—About 47 cm.

*Lateral branches.*—Length: About 36 cm. Diameter: About 6 mm. Internode length: About 2.3 cm. Aspect: Upright and outwardly spreading. Strength: Strong. Texture: Sparsely pubescent. Color: 146C.

*Foliage description.*—Arrangement: Alternate; simple. Length: About 5.5 cm. Width: About 2.3 cm. Shape: Elliptic to obovate with protruding points. Apex: Acute. Base: Attenuate. Margin: Entire with six protruding points. Venation pattern: Pinnate. Texture, upper and lower surfaces: Smooth, glabrous; coarse; glandular. Color: Developing foliage, upper and lower surfaces: 147A; venation, 147B. Fully expanded foliage, upper and lower surfaces: 147A; venation, 147C. Petiole: Length: About 1.5 cm. Diameter: About 5 mm. Texture, upper and lower surfaces: Glabrous, smooth. Color, upper and lower surfaces: 146B.

Inflorescence description:

*Appearance.*—Solitary terminal and axillary inflorescences held above and beyond the foliage on strong peduncles. Composite inflorescence form, radially symmetrical, with ligulate-shaped ray florets and disc florets massed at the center; ray and disc florets develop acropetally on a capitulum. Inflorescences persistent. Inflorescences face mostly upright to outwardly.

*Flowering response.*—Plants flower continuous and freely from the spring through the fall.

*Postproduction longevity.*—Inflorescences maintain good color and substance for about four to six days on the plant.

*Quantity of inflorescences.*—Freely flowering; at one time, about four to six open inflorescences and inflorescence buds per lateral stem.

*Fragrance.*—None detected.

*Inflorescence bud.*—Length: About 2.5 cm. Diameter: About 1.4 cm. Shape: Ovoid, elongate. Color: More gray than 79C.

*Inflorescence size.*—Diameter: About 7.4 cm. Depth (height): About 2.3 cm. Disc diameter: About 1.8 cm. Receptacle height: About 1.6 cm. Receptacle diameter: About 2.5 cm.

*Ray florets.*—Length: About 3.8 cm. Width: About 8 mm. Shape: Elliptic to ligulate. Apex: Slightly emarginate. Base: Attenuate. Margin: Entire. Texture, upper and lower surfaces: Smooth, glabrous; velvety. Orientation: Initially upright then about 60° from vertical and apices reflexed. Number of ray florets per inflorescence: About 20 in a single whorl. Color: When opening, upper surface: 77B. When opening, lower surface: Alternating longitudinal stripes of 79C, 79D, 83B and 79A; towards the margin, 77B. Fully opened, upper surface: Alternating longitudinal stripes of 77B and 77C; color becoming closer to 77C and 77D with development. Fully opened, lower surface: Alternating longitudinal stripes of 79A, 79C and 202C; towards the margin, 85A.

*Disc florets.*—Shape: Tubular, elongated. Apex: Five-pointed. Length: About 1 cm. Width: At apex: About 5 mm. At base: About 1 mm. Number of disc florets per inflorescence: About 80. Color: Immature: 157A. Mature: Apex: 157B. Mid-section and base: 157D.

*Phyllaries.*—Length: About 1.3 cm. Diameter: About 3 mm. Shape: Lanceolate. Apex: Acuminate. Base: Fused. Margin: Entire. Texture, upper and lower surfaces: Sparsely pubescent; slightly coarse. Number per inflorescence: About 16 in a single whorl. Color, upper surface: 146B. Color, lower surface: 146A.

*Peduncles.*—Length, terminal peduncle: About 21.5 cm. Length, second peduncle: About 24.5 cm. Length, third peduncle: About 19 cm. Diameter: About 2.5 mm. Angle: Terminal peduncles, mostly upright; axillary peduncles about 45° from stem axis. Strength: Strong. Texture: Sparsely pubescent; slightly coarse; glandular. Color: 144A.

*Reproductive organs.*—Androecium: Present on disc florets only. Stamen number: Five per floret; fused around style. Anther shape: Oblong. Anther size: About 1 mm by 3 mm. Anther color: Apex, 79A; mid-section and base, 14C. Pollen amount: Scarce. Pollen color: 23A. Gynoecium: Present on both ray and disc florets. Pistil number: One per floret. Pistil length: About 8 mm. Stigma shape: Two-parted. Stigma color: 79B. Style length: About 4 mm. Style color: 79B to 79C. Ovary color: 145A.

*Seed/fruit.*—Seed and/or fruit production has not been observed.

Disease/pest resistance: Resistance to pathogens and pests common to *Osteospermums* has not been observed on plants grown under commercial greenhouse or outdoor conditions.

Temperature tolerance: Plants of the new *Osteospermum* have been observed to tolerate temperatures from 4° C. to 35° C.

It is claimed:

1. A new and distinct cultivar of *Osteospermum* plant named 'Mt. Dandenong', as illustrated and described.

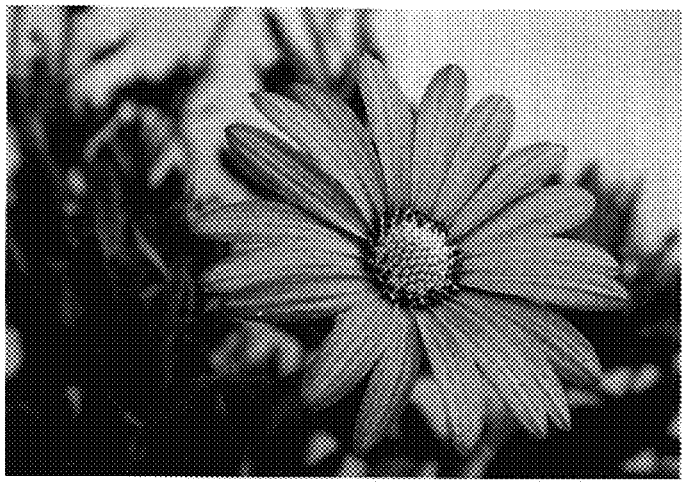
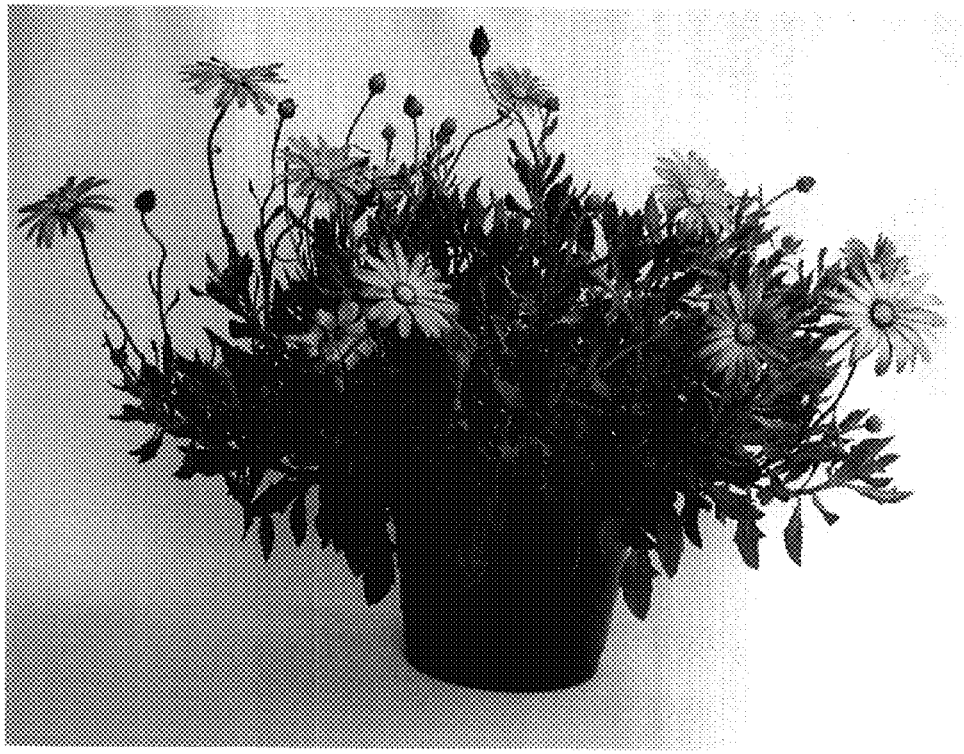

* * * * *